United States Patent [19]
Savins et al.

[11] 4,087,936
[45] May 9, 1978

[54] PROCESS FOR PRODUCTION OF ALGA BIOPOLYMER AND BIOMASS

[75] Inventors: Joseph George Savins; Maynard L. Anderson, both of Dallas, Tex.

[73] Assignee: Mobil Oil Corporation, New York, N.Y.

[21] Appl. No.: 750,089

[22] Filed: Dec. 13, 1976

[51] Int. Cl.$^2$ .......................... A01G 7/00; C02C 1/00
[52] U.S. Cl. ...................................................... 47/1.4
[58] Field of Search ............................................ 47/1.4

[56] References Cited

U.S. PATENT DOCUMENTS

| | | | |
|---|---|---|---|
| 3,362,104 | 1/1968 | Oswald et al. | 47/1.4 |
| 3,889,418 | 6/1975 | Porter et al. | 47/1.4 X |
| 3,958,364 | 5/1976 | Schenck et al. | 47/1.4 |
| 3,969,844 | 7/1976 | Fogel et al. | 47/1.4 X |
| 4,005,546 | 2/1977 | Oswald | 47/1.4 |

Primary Examiner—Robert E. Bagwill
Attorney, Agent, or Firm—C. A. Huggett; William D. Jackson

[57] ABSTRACT

This specification discloses a process for the production of alga biopolymer and alga biomass. The first step of the process is carried out in a seed reactor. In this step, an aqueous culture containing an inoculum of alga and nutrients required for the growth of the alga is subjected to artificial illumination of an intensity and for such a time as to initiate growth of the alga. The aqueous culture is also subjected to the action of a mixture of carbon dioxide and air during this first step. After growth of the alga is initiated, at least a portion of the alga biomass is transferred to a main reactor where the second step of the process is carried out. In this step, the alga biomass in an aqueous culture is subjected to artificial illumination of an intensity and duration to effect growth of alga biomass and, concomitantly, synthesis of alga biopolymer. It is also subjected to the action of a mixture of carbon dioxide and air. During this second step the aqueous culture containing the alga biomass may be additionally subjected to the action of solar radiation. Following the second step, alga biomass is separated from the aqueous culture which contains extracellular biopolymer. The alga biopolymer can be subjected to a variety of uses. The biomass, if desired, may be treated for recovery of intracellular biopolymer and the resultant biomass sludge subjected to a variety of uses.

24 Claims, 1 Drawing Figure

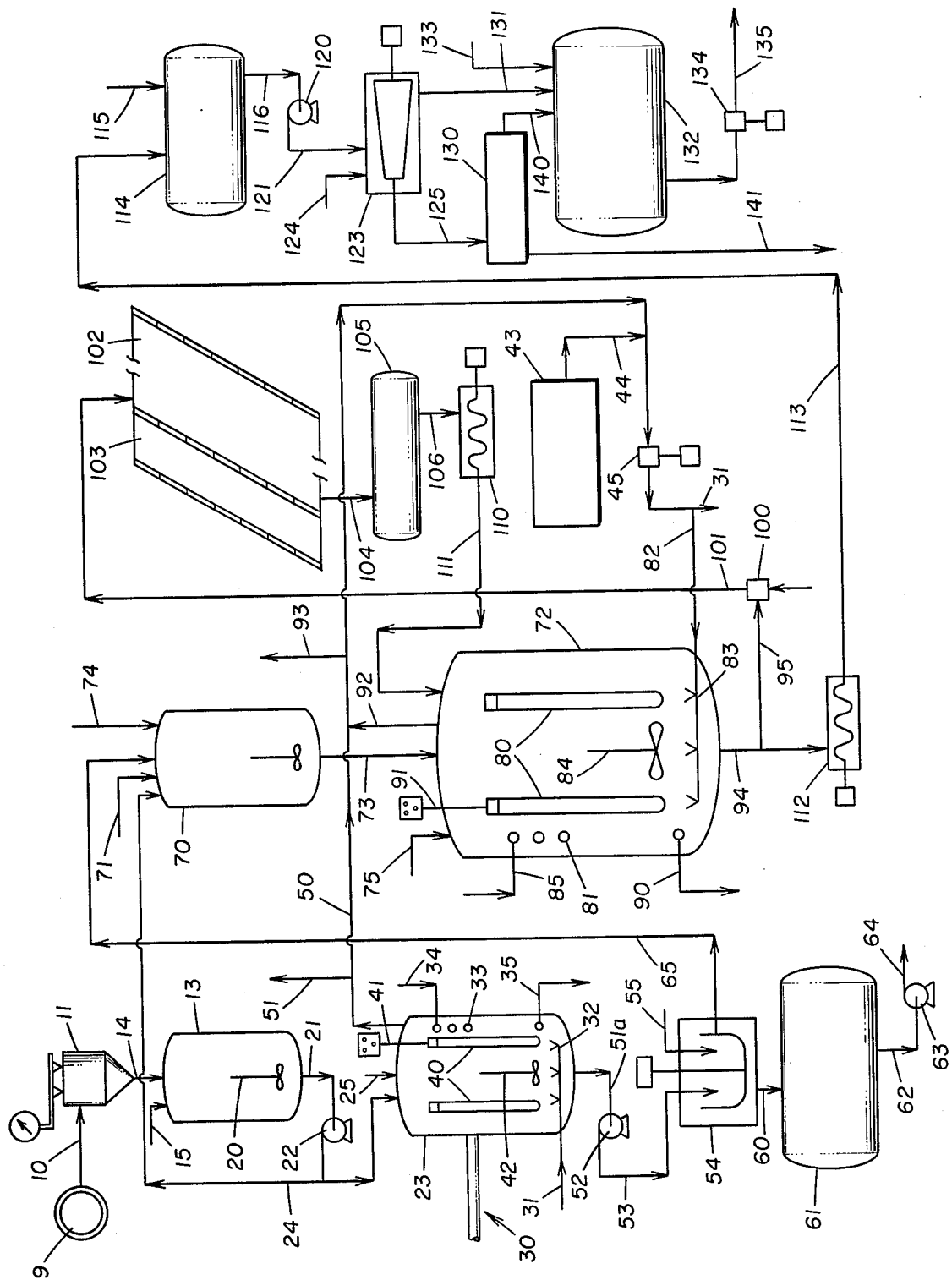

PROCESS FOR PRODUCTION OF ALGA BIOPOLYMER AND BIOMASS

BACKGROUND OF THE INVENTION

1. Field of the Invention

The invention relates to the production of alga biomass and alga biopolymer.

2. Description of the Prior Art

Processes for the growth of alga are well known. For example, U.S. Pat. No. 3,195,271 discloses a process for the growth of the alga *Porphyridium cruentum* and synthesis of the alga constituent carrageenin. Other processes for the growth of alga are disclosed in "Algal Culture: From Laboratory to Pilot Plant," J. S. Burlew, Ed., Carnegie Inst. of Washington, Publication No. 600, Washington, D.C. (1964), and "Properties and Products of Algae", J. E. Zajic, Ed., Plenum Press, N.Y. (1970). A culture for the growth of the alga *Porphyridium aerugineum*, known as the MCYII medium, is disclosed by Ramus, J., in the *Jnl. Phycol.*, 8 [1], 97 (1972) and by Gantt, E. et al., in the *Jnl. Phycol.*, 4, 65 (1968). The influence of light quality on the production of algal biomass production is disclosed in "Spectral Light Requirements of Algae," Brown, T. E., Tech. Report No. 69-45-FL, U.S. Army Natick Labs., October, 1968.

SUMMARY OF THE INVENTION

The invention provides a process for the growth of alga biomass and concomitant synthesis of alga bipolymer. The process is carried out in two steps. In the first step, an aqueous culture containing an inoculum of alga and contained in a seed reactor is subjected to artificial illumination of such intensity and for such time that growth of the alga is initiated. The aqueous culture contains nutrients required for growth of the alga and during the first step is subjected to the action of mixture of carbon dioxide and air. After growth of the alga has been initiated, at least a portion of the alga biomass is removed from the seed reactor and transferred to a main reactor where the second step is carried out. In the second step, the alga biomass in an aqueous culture containing nutrients required for growth of the alga is subjected to artificial illumination of such intensity and such duration as to effect growth of the alga and concomitantly, synthesis of biopolymer. During this second stage, the aqueous culture is also subjected to the action of a mixture of carbon dioxide and air. Further, during this second stage, a portion of the aqueous culture may be subjected to natural illumination. Following the second step, the alga biomass is separated from the aqueous culture which also contains extracellular alga biopolymer. The alga biomass may be treated for recovery of intracellular bipolymer and the resultant biomass sludge subjected to a variety of uses. The aqueous culture containing the extracellular biopolymer may be employed per se for such use as is desired for the biopolymer. Alternatively, the extracellular biopolymer may be recovered from the aqueous culture, and also may be combined with the intracellular biopolymer, for such use as is desired.

BRIEF DESCRIPTION OF THE DRAWINGS

The FIGURE is a flowsheet schematically illustrating the process of the invention.

DESCRIPTION OF THE PREFERRED EMBODIMENTS

Many algae, during their life cycle in a culture, synthesize biopolymers. These biopolymers are synthesized within the alga cell. They are transported to the surface of the cell and can dissolve from the surface of the cell and enter into solution in the culture. The biopolymers when within the cell are termed intracellular biopolymers and after leaving the cell are termed extracellular biopolymers. The extracellular biopolymers may be of a viscous nature thus imparting thickening to an aqueous medium containing them. Various uses for these biopolymers are known to the art. Recently, they have been proposed as a thickening agent for aqueous driving fluids employed for the recovery of petroleum from a subterranean petroleum-containing formation. The alga biomass also has various uses.

The present invention is directed to a method for the growth of alga biomass and the concomitant synthesis of biopolymer. The biopolymer may be employed as a thickening agent in aqueous driving fluids for the recovery of petroleum from a subterranean petroleum-containing formation. However, the biopolymer may also be employed otherwise as is known to the art. The biomass, which may have the intracellular biopolymer removed therefrom, may be employed as a feed substrate for biodegradation by selected microorganisms, including bacteria and yeasts and converted to a variety of products, including methane and alcohol. The biomass is rich in protein and may also be allocated for use as feed for terrestrial agricultural or mariculture operations.

The method of the invention may be employed for the growth of, and synthesis of biopolymer from, various algae. Such alga may be from the divisions Chlorophyta, Phaeophyta, Rhodophyta, and Cyanophyta. In the division Chlorophyta, they may be from the genus Ulva. In the division Phaeophyta, they may be from the genera Ilea and Pelvetiopsis. In the division Rhodophyta, they may be from the genera Porphyra, Corallina, Gratelupia, Gymnogongrus, Stenogramma, and Rhodemenia. In the division Cyanophyta, they may be from the genus Anabaena. In the genus Porphyra, they may be the species *Porphyridium aerugineum* or *Porphyridium cruentum*. In the genus Anabaena, they may be the species *Anabaena flos-aquae*. In the division Chlorophyta, they may be the species *Chlorella stigmataphora*. Preferably, the method and apparatus of the invention is employed for the synthesis of biopolymer from the species *Porphyridium aerguineum*.

Algae, including *Porphyridium aerugineum*, as is known, require for their growth water, illumination—i.e. radiant energy, a carbon source, and certain other nutrients and nutrient-related materials. The illumination may be sunlight, i.e. solar radiation, or, also as known, may be a prescribed bandwidth of artificial illumination. In the method of the invention, artificial illumination is employed in the first and second steps. In the second step, solar radiation may be employed additionally to the artificial radiation. With algae which are obligate photoautotrophs, such as *Porphyridium aerugineum*, the source of carbon is customarily gaseous carbon dioxide. The gaseous carbon dioxide is normally supplied in admixture with air. The nutrients and nutrient-related materials are exemplified by the components, in addition to water, contained in the MCYII medium previously mentioned. This medium contains the distribution of macro and micro levels of inorganic ions, chelating agents, buffering agent, etc. set forth in Table I.

TABLE I

| MCYII MEDIUM | |
|---|---|
| Component | Amount |
| $NaNO_3$ | 442 mg |
| KCl | 30 mg |
| $CaCl_2 \cdot 2H_2O$ | 36.6 mg |
| $FeCl_3 \cdot 6H_2O$ | 1.9 mg |
| $MgSO_4 \cdot 7H_2O$ | 100 mg |
| $Na_2 \cdot$ glycerophosphate $\cdot 5H_2O$ | 90 mg |
| Tricine buffer | 986 mg |
| PII trace metal mix | 10 ml |
| Vitamin $B_{12}$ | 3.5 µg |
| Distilled water to | 1000 ml |
| Adjust pH to 7.6 with NaOH | |
| PII Metal Mix: | |
| $H_3BO_3$ | 114.0 mg |
| $MnCl_2 \cdot 4H_2O$ | 14.4 mg |
| $ZnSO_4$ | 2.2 mg |
| $CoCl_2 \cdot 6H_2O$ | 0.44 mg |
| $FeCl_3 \cdot 6H_2O$ | 4.8 mg |
| $Na_2EDTA$* | 100 mg |
| Distilled water to | 100 ml |

*Disodium salt of ethylene diamine tetraacetic acid.

Other nutrients and nutrient-related materials are exemplified by the components, in addition to water, contained in another medium identified as the "Modified MCYII Medium." These components are set forth in Table II below.

TABLE II

| Modified MCYII Medium | |
|---|---|
| Component | Amount |
| $MgSO_4 \cdot 7H_2O$ | 100 mg |
| $NaNO_3$ or | 442 mg |
| Urea | 155 mg |
| $CaCl_2$ | 28 mg |
| $FeCl_3$ or | 1.43 mg |
| $C_{10}H_{12}FeN_2NaO_8$ | 5.36 mg |
| $K_2HPO_4$ or | 51 mg |
| $Na_2HPO_4$ | 42 mg |
| $H_3BO_3$ | 11.4 mg |
| $FeSO_4 \cdot 7H_2O$ | 2.2 mg |
| $ZnSO_4 \cdot 7H_2O$ | 1.44 mg |
| KCl | 30 mg |
| $B_{12}$ | $3.5 \times 10^{-6}$ mg |
| $CoCl_2 \cdot 6H_2O$ | 0.044 mg |
| $(Na)_2EDTA$ | 10 mg |
| Distilled water to | 1000 ml |

The MCYII medium, the Modified MCYII medium, or other suitable medium, may be employed in the method of the invention.

In the first step of the invention, an aqueous culture containing an inoculum of alga is subjected in a seed reactor to artificial illumination of such intensity and for such time that growth of the alga is initiated. In the second step of the invention, after growth of the alga has been initiated, an aqueous culture of the growing alga is subjected to artificial illumination and, if desired, to additional solar radiation, of such intensity and for such time to effect additional growth of the alga biomass and synthesis of biopolymer. It has been discovered by one of us, Joseph George Savins, that in the growth of alga biomass and synthesis of alga biopolymer four radiant energy-related design parameters are involved. These parameters are as follows: (1) $\psi_a$, an "intrinsic slope" or the initial linear gradiant of the cumulative absorbed radiant energy versus time curve evaluated over the initial period of $0 < t < 2$ days; (2) $\theta_l$, a lag time preceding the phase of rapid growth of alga biomass and synthesis of biopolymer; (3) $(E_a)_c$, the cumulative moles of radiant energy quanta absorbed by the illuminated culture; and (4) the group $\psi_a/(E_a)_c$.

The "lag time" is herein defined as the phase of growth of the alga biomass preceding the phase of rapid growth, or log phase of growth, of the alga biomass. During the lag time there is slow but significant growth of the alga biomass. In the two steps of the process of the invention, the first, third, and fourth radiant energy-related parameters mentioned above are manipulated to obtain a minimum lag time preceding growth of the alga, i.e., the second parameter, and to obtain a maximum rate of growth of biomass and synthesis of biopolymer and to obtain a maximum ratio of extracellular biopolymer to biomass.

From the standpoint of synthesis of biopolymer, control of the three parameters has the particular advantage of combining a rapid rate of synthesis of the biopolymer with economy of synthesis and is based upon four observations. The first observation is that the lag time preceding the onset of biopolymer synthesis in a culture of alga correlates with the rate of absorption of radiant energy in the culture during the early stage of growth, i.e., the higher the rate of absorption, the smaller the lag time. The second observation is that the efficiency of biopolymer synthesis, i.e.

$$100 \left[ \frac{\text{chemical energy of biopolymer formed}}{\text{photochemical equivalents absorbed}} \right],$$

correlates with the rate of absorption of the radiant energy during the lag time, the greater the rate of absorption, the greater the efficiency. The third observation is that the amount of biopolymer synthesized is a function of the cumulative energy absorbed during the reaction time, the higher the cumulative energy absorbed, the greater the amount of biopolymer synthesized. The fourth observation is that the biopolymer synthesis, once "triggered" or initiated in the first step, continues into the second step.

In the process, by employing artificial illumination in the first step, and with control of the three radiant energy-related parameters, the lag time is decreased. Therefore, to the extent that the lag time is decreased, the time required to obtain a desired amount of biomass and biopolymer is decreased and efficiency of production is increased. Further, since the biopolymer synthesis, after having once been "triggered" in the first step, continues into the second step which can employ solar radiation in addition to artificial illumination, the economy of employing the solar radiation is obtained. Additionally, the ratio of biopolymer to biomass is maximized.

In the synthesis of *Porphyridium aerugineum* biomass and biopolymer, the first step of the process is carried out employing continuous artificial illumination of such intensity that $\psi_a$ is about 0.33 Einstein (0.0165 kilowatt-hour) per day per liter of culture and for such a time that $(E_a)_c$ is between about 0.66 to 0.89 Einstein (0.33 to 0.045 kw-hr) per liter of culture. With these values of the two parameters, the lag time $(\theta_l)$ will be about 40 hours. For the two steps of the process, the value of $(E_a)_c$ should be between about 1.2 and 2.0 Einsteins (0.060 and 0.100 kw-hr) per liter and the value of $\psi_a/(E_a)_c$ should be about 0.18 per day.

Further, in the process of the invention, in the first and second steps thereof, the artificial illumination may be enriched with respect to particular wavelengths. Where the alga is *Porphyridium aerugineum*, the illumination may have its energy content predominantly in the region of about 600 to 700 nanometers. By "predominantly" is meant that at least 50 percent of the energy in the illumination is in the region of about 600 to 700 nanometers.

Reference will now be made to the drawing for a detailed description of one specific embodiment of the invention.

Solid nutrients for use in an aqueous culture for the growth of alga biomass and biopolymer, such as the nutrients employed in the cultures set forth in Tables I and II preceding, are transferred from drum 9 through line 10 to weigh hopper 11. Each of the nutrients in the proper amount is then transferred to mix tank 13 through line 14. Water is added to the mix tank 13 from line 15 in sufficient amount such that the nutrients constitute 10 percent by weight of the resulting solution. The mix tank 13 is provided with mixer 20 to assist in solution of the nutrients in the water. The nutrient concentrate is pumped from the mix tank through line 21 by pump 22 to seed reactor 23 through line 24 and water is added to the nutrient concentrate through line 25 in sufficient amount to obtain the desired concentration for growth of alga biomass and synthesis of biopolymer. At the beginning of operations, an inoculum of the desired alga is passed into the seed reactor through line 30. However, since, as mentioned above, growth of biomass will occur during the lag time, following the beginning of operations the inoculum of the alga is provided by retaining a portion of the previous batch in the seed reactor.

The seed reactor 23 is provided with inlet line 31 and sparger 32 for passage of a mixture of carbon dioxide and air into contact with the aqueous culture of alga in the reactor. It is also provided with a cooling coil 33 through which refrigerant brine flows from inlet line 34 to outlet line 35. It is further provided with illuminators 40 to which electrical current is supplied through line 41. A suitable type of illuminator is a source which provides light of a quality rich in a bandwidth of wavelengths which favors maximum biomass production. These are known to the art. The seed reactor is additionally provided with mixer 42.

In the seed reactor 23, the aqueous culture is subjected to action of the artificial illumination from the illuminators. Simultaneously, a mixture of carbon dioxide and air is injected through the line 31 and spargers 32 into the aqueous culture. The mixture of carbon dioxide and air is provided from gas generator 43 and pumped therefrom through line 44 by pump 45. Agitation is further provided in the seed reactor by mixer 42. The illumination provided by the illuminators 40 is of such intensity and is continued for such time, along with injection of the mixture of carbon dioxide and air, that growth of the alga is initiated, i.e., is continued during the entire lag time or until rapid growth of the alga biomass begins to occur. As indicated, with the alga *Porphyridium aerugineum* a lag time of about 40 hours can be expected when the illumination is about 0.33 Einstein (0.0165 kw-hr) per day and the total illumination is about 0.66 to 0.89 Einstein (0.033 to 0.045 kw-hr) per liter of culture.

Off gas from the seed reactor 23 is removed through line 50 and a portion is vented through line 51 connected to line 50. The remainder is recycled through the line 50 to be added to the gas pumped from the generator 43 by the pump 45. Waste heat from the illuminators is removed by the cooling coil 33 by circulating refrigerant brine therethrough to maintain the reaction temperature at approximately 76° F. (24.4° C.). When growth of the alga biomass has been initiated, a portion of the aqueous culture is removed from the seed reactor 23, the remainder being kept in the seed reactor as inoculum for the next batch of aqueous culture. Normally, about one-half of the aqueous culture is removed from the seed reactor.

The aqueous culture containing the alga biomass is removed from the seed reactor 23 through line 51A and pumped by pump 52 through line 53 to basket centrifuge 54. In the basket centrifuge, the alga biomass is separated from the aqueous solution of nutrients and is washed with water from line 55. The wash water, and the aqueous solution of nutrients from which the alga biomass was separated, are passed through line 60 to slop tank 61 from which they may be pumped through line 62 by pump 63 through line 64 to an appropriate disposal system. The washed biomass is discharged from the centrifuge through line 65 to transfer drum 70.

In the transfer drum, the washed alga biomass is mixed with water entering through line 71 and with nutrient-concentrate solution pumped by pump 22 through line 24. The resultant aqueous culture of the alga is then transferred to main reactor 72 through line 73 by means of air pressure from line 74 where it is mixed with water entering through line 75. The amounts of water and nutrient concentrate mixed with the alga biomass in the transfer drum 70 and the amount of water added to the main reactor 72 are such that the resulting mixture contains the proper concentration of nutrients for growth of the alga.

The main reactor 72 is provided with illuminators 80, cooling coil 81, inlet line 82 and spargers 83 for a mixture of carbon dioxide and air, and mixer 84, similarly as the seed reactor. The cooling coil is provided with inlet line 85 and outlet line 90 for refrigerant brine and the illuminators are provided with electrical current through electrical supply line 91. These illuminators may be similar to illuminators 40. In the main reactor, the aqueous culture is agitated and subjected to artificial illumination of such intensity and for such time, along with the action of a mixture of carbon dioxide and air, for such time that the desired extent of growth of alga biomass and synthesis of biopolymer is obtained. With *Porphyridium aerugineum* the intensity and time of the illumination should be such that the total radiant energy absorbed, i.e., that absorbed in the seed reactor and that absorbed in the main reactor, is about 1.2 and 2.0 Einsteins (0.060 and 0.100 kw-hr) per liter and the value of $\psi_a/(E_a)_c$ is at least about 0.18 per day.

Off gas from the main reactor 72 is removed through line 92 and a portion is vented through line 93. The remainder is recycled to be mixed with the gas mixture pumped by pump 45. Waste heat from the illuminators is removed by the cooling coil 81 by circulating refrigerant brine therethrough to maintain the reaction temperature at approximately 76° F. (24.4° C.). Agitation additional to that provided by the mixture of carbon dioxide and air is provided by the mixer 84.

The entire amount of illumination supplied to the aqueous culture of the alga in the main reactor may be provided by the illuminators. Alternatively, a portion of the illumination may be provided by solar radiation. For this purpose, during daylight hours aqueous culture is removed from the main reactor through lines 94 and 95 and is pumped by air lift pump 100 through line 101 to natural illuminators 102 exposed to solar radiation. Air lift pumping is employed in this portion of the operation to minimize destruction of the alga biomass which is shear sensitive. The natural illuminator comprises a plurality of inclined parallel reactors 103 and the aqueous culture is distributed to the reactors via a manifold (not shown). The aqueous culture flows down the illuminator as a film and is periodically redistributed by baffles (not shown) to prevent channeling. A transparent plastic film (not shown) covers the illuminator to prevent contamination of the aqueous culture. The aqueous culture is collected in a manifold (not shown) at the bottom of the illuminator and drained through line 104 to recycle drum 105. From the recycle drum the aqueous culture is removed through line 106 and pumped by pump 110 through line 111 to the main reactor 72. Pump 110 is a low shear pump such as a Moyno pump. Two-volume transfers of the aqueous culture from the main reactor to the natural illuminator may be made each 12-hour period of light per day. Residual heat from the solar radiation is removed by the cooling coil 81 in the main reactor. Pumping of the aqueous culture to the natural illuminator is discontinued during nighttime hours.

When growth of the alga biomass and biopolymer is completed in the main reactor, the aqueous culture is removed from the main reactor through line 92 and is pumped by low shear pump 112, which may be a Moyno pump, through line 113 to hold-up drum 114. Water may be added to the aqueous culture in the hold-up drum through line 115 to reduce the concentration of the biopolymer. The contents of the hold-up drum are removed continuously through line 116 and pumped by pump 120 through line 121 to solid bowl centrifuge 123. In the centrifuge, the biomass is separated and washed with water entering the centrifuge through line 124. The washed biomass is removed from the centrifuge through line 125 and passed to separator 130.

The supernatant from the centrifuging operation in the centrifuge 123, which is a viscous solution of the extracellular alga biopolymer, along with the wash water, is removed from the centrifuge through line 131. From line 131, the viscous supernatant may be transported by rail car, tank truck, pipeline or other suitable means to a site where it is to be used. For example, it may be transported to the site of a waterflooding operation for the recovery of petroleum from a subterranean petroleum-containing formation wherein thickened aqueous driving fluid is employed for the recovery of the petroleum. At the site the biopolymer is employed as the thickening agent, being diluted, if required, to the proper viscosity for recovery of the petroleum. Alternatively, the supernatant, along with the wash water removed from the centrifuge through line 131, is sent to biopolymer solution storage tank 132. In the tank 132, the viscosity of the biopolymer solution may be reduced by addition of water entering through line 133 to a level satisfactory for use in a waterflooding operation employing thickened aqueous driving fluid for the recovery of petroleum from a petroleum-containing subterranean formation. The solution of biopolymer may then be pumped by pump 134 through line 135 to the site of the waterflooding operation.

Alternatively, the biopolymer may be precipitated from the culture by the addition of an alcohol such as isopropanol. The precipitated biopolymer may then be separated by centrifugation or filtration from the supernatant culture and dried under mild drying conditions for storage, transportation, or otherwise. The dried biopolymer may be used as the thickening agent in the aqueous driving fluid. However, reconstitution of the dried biopolymer by the addition thereto of water results in a loss of thickening ability. In other words, the viscosity of a solution of the reconstituted biopolymer is less than that of an in-vivo solution culture containing the same amount of the biopolymer. Accordingly, the biopolymer may be centrifuged to remove cells and then precipitated by addition of an alcohol but loss of performance avoided by not drying the product, instead suspending it in a suitable liquid which will not hydrate the biopolymer, as for example an alcohol, and transporting in a non-hydrated slurry form by rail, truck, pipeline, or other suitable means to a site where it is to be used. There the viscous system is recovered by adding water back to the slurry, allowing the particles to rehydrate, and adjusting the viscosity to a level satisfactory for use as a mobility control slug in an enhanced oil recovery process.

Alternatively, the biopolymer may be "upgraded" with respect to certain characteristics for the purpose of enhancing its use in mobility control. For example, there is a need for improvements in "flow resistance" materials in waterflooding processes which reduce fingering and improve producing characteristics of wells which exhibit rapid water and thickener breakthrough and in so doing aggravate emulsion treating problems in surface equipment. In this aspect of the invention, the supernatant or in-vivo form of the alga biopolymer is complexed with a heavy metal or transition metal ion, such as trivalent chromium to form a material with improved flow resistance characteristics.

The alga biomass in separator 130 is sacrificed and intracellular biopolymer recovered and separated from the resulting biomass sludge. The intracellular biopolymer is removed from the separator through line 140 and passed to the storage tank 132 where it is handled as described above for the extracellular biopolymer. The biomass sludge is removed from the separator through line 141 and allocated as a feed substrate for biodegradation by selected organisms, including bacteria and yeasts, and converted to a variety of products, including methane and alcohol. The protein-rich sludge may also be allocated for use as feed for terrestrial agriculture or mariculture operations.

The following equipment sizes and amounts of equipment will provide a production rate of 500,000 pounds (226,795 kilograms) per year of biopolymer. Two mix tanks 13 each of 1,000 gallons (3.79 cubic meters) will be required. Three seed reactors each of 10,000 gallons (37.9 cubic meters) will also be required. One basket centrifuge 54, one slop tank 61 of 10,000 gallons (37.9 cubic meters) capacity, one transfer drum 70 of 5,000 gallons (18.95 cubic meters) capacity, one natural illuminator 102 of 380,000 feet$^2$ (35,302 square meters) in area, one recycle drum 104 of 15,000 gallons (56.85 cubic meters) capacity, one gas generator 43, ond centrifuge 123, and one separator 130 will be sufficient. However, 15 main reactors 72 of 50,000 gallons (189.5 cubic meters) capacity, two hold-up drums 14 of 25,000 gallons (94.75 cubic meters) capacity and two storage tanks 132 of 40,000 gallons (151.2 cubic meters) capacity will be required. As to pumps, two pumps 22, one pump 45, three pumps 52, two pumps 63, one air-lift pump 100, three pumps 110, two pumps 112, two pumps 120, and one pump 134 will be required.

We claim:

1. A process for the production of alga biopolymer and alga biomass comprising as a first step subjecting, in a seed reactor in the presence of a mixture of carbon dioxide and air, an aqueous culture containing an inoculum of alga and nutrients required for the growth of said alga to the action of artificial illumination of an intensity and for such a time to initiate growth of said alga, transferring at least a portion of said alga culture from said seed reactor to a main reactor, as a second step subjecting, in said main reactor in the presence of a mixture of carbon dioxide and air, an aqueous culture containing said alga and nutrients required for the growth of said alga to the reaction of artificial illumination of an intensity and for such a time to effect growth of alga biomass and concomitantly synthesis of alga biopolymer, and during said first and second steps manipulating the linear gradient of the cumulative absorbed radiant energy from the illumination versus time curve over the initial period of $0 < t < 2$ days, $\psi_a$, the cumulative absorbed moles of radiant energy quanta from the illumination, $(E_a)_c$, and the ratio $\psi_a/(E_a)_c$.

2. The process of claim 1 wherein in said second step said aqueous culture is additionally subjected to the action of solar radiation.

3. The process of claim 2 wherein said aqueous culture is additionally subjected to the action of solar radiation by circulating aqueous culture from said main reactor through an illuminator exposed to solar radiation.

4. The process of claim 1 wherein said alga is *Porphyridium aerugineum*.

5. The process of claim 4 wherein $\psi_a$ is about 0.33 Einstein (0.0165 kw-hr) per day per liter of culture, $(E_a)_c$ between about 1.2 and 2.0 Einsteins (0.060 and 0.100 kw-hr) per liter of culture, and $\psi_a/(E_a)_c$ is about 0.18 per day.

6. The process of claim 5 wherein said artificial illumination has its energy content predominantly in the region of about 600 to 700 nanometers.

7. The process of claim 4 wherein during said first step $\psi_a$ is about 0.33 Einstein (0.0165 kw-hr) per day per liter of culture and $(E_a)_c$ is between about 0.66 and 0.89 Einstein (0.033 and 0.045 kw-hr) per liter of culture.

8. The process of claim 7 wherein said artificial illumination has its energy content predominantly in the region of about 600 to 700 nanometers.

9. The process of claim 1 wherein said artificial illumination in said first and second steps is enriched with respect to particular wavelengths.

10. The process of claim 9 wherein said alga is *Porphyridium aerugineum*.

11. The process of claim 10 wherein said artificial illumination has its energy content predominantly in the region of about 600 to 700 nanometers.

12. A process for the production of alga biopolymer and biomass comprising mixing water and nutrients required for the growth of alga in a mixing tank to provide a concentrated nutrient solution, transferring said concentrated nutrient solution to a seed reactor, diluting said concentrated nutrient solution in said seed reactor with water and adding thereto an inoculum of alga to form an aqueous culture for the growth of said alga, subjecting said aqueous culture in said seed reactor to the action of a mixture of carbon dioxide and air, simultaneously therewith subjecting said aqueous culture to artificial illumination of an intensity and for a time to initiate growth of said alga, maintaining said aqueous culture at a temperature suitable for the growth of said alga, thereafter removing a portion of said aqueous culture from said seed reactor, replacing said portion of said aqueous culture removed from said seed reactor with an equal volume of water and concentrated nutrient solution to form an aqueous culture for the growth of said alga contained therein, subjecting said aqueous culture in said seed reactor to the action of a mixture of carbon dioxide and air, simultaneously therewith subjecting said aqueous culture to artificial illumination of an intensity and for such time to initiate growth of said alga, periodically repeating the steps of removing a portion of said aqueous culture from said seed reactor, replacing it with an equal volume of water and concentrated nutrient solution to form an aqueous culture for the growth of said alga contained therein, subjecting it to the action of a mixture of carbon dioxide and air, simultaneously therewith subjecting it to artificial illumination of an intensity and for such time to initial growth of said alga and maintaining it at a temperature for growth of said alga, separating alga biomass from said aqueous culture removed from said seed reactor, transferring said alga biomass to a transfer drum, adding to said biomass in said transfer drum water and concentrated nutrient solution, transferring the resulting mixture to a main reactor, adding to said resulting mixture in said main reactor water in an amount to form an aqueous culture for the growth of said alga contained therein, subjecting said aqueous culture in said main reactor to the action of a mixture of carbon dioxide and air, simultaneously therewith subjecting said aqueous culture to the action of artificial illumination of such intensity and for a time to effect growth of said alga, maintaining said aqueous culture at a temperature suitable for the growth of said alga, transferring said aqueous culture from said main reactor after growth of said alga has been completed to a hold-up tank, removing said aqueous culture from said hold-up tank, and centrifuging said aqueous culture to separate alga biomass from supernatant solution containing alga biopolymer.

13. The process of claim 12 wherein, during growth of said alga in said main reactor, a stream of aqueous culture is removed from said main reactor, passed to a natural illuminator and subjected to solar radiation, and returned to said main reactor.

14. The process of claim 12 wherein said biopolymer is transferred to a biopolymer storage tank and thereafter tranported to a site from which it is injected into a subterranean petroleum-containing formation for the recovery therefrom of petroleum.

15. The process of claim 12 wherein said alga biomass is sacrificed for recovery therefrom of intracellular biopolymer.

16. The process of claim 12 wherein said alga is *Porphyridium aerugineum*.

17. The process of claim 12 wherein the illumination is manipulated as to the linear gradient of the cumulative absorbed radiant energy versus time curve over the initial period of $0 < t < 2$ days, $\psi_a$, the cumulative absorbed moles of radiant energy, $(E_a)_c$, and the ratio of $\psi_a/(E_a)_c$.

18. The process of claim 17 wherein $\psi_a$ is about 0.33 Einstein (0.0165 kw-hr) per day per liter of culture, $(E_a)_c$ is between about 1.2 and 2.0 Einsteins (0.060 and 0.100 kw-hr) per liter of culture, and $\psi_a/(E_a)_c$ is about 0.18 per day.

19. The process of claim 18 wherein said artificial illumination has its energy content predominantly in the region of about 600 to 700 nanometers.

20. The process of claim 17 wherein, in said seed reactor, the illumination is such that $\psi_a$ is about 0.33 Einstein (0.0165 kw-hr) per day per liter of culture and $(E_a)_c$ is between about 0.66 and 0.89 Einstein (0.033 and 0.045 kw-hr) per liter of culture.

21. The process of claim 20 wherein said artificial illumination has its energy content predominantly in the region of about 600 to 700 nanometers.

22. The process of claim 12 wherein said aritificial illumination in said first and second steps is enriched with respect to particular wavelengths.

23. The process of claim 22 wherein said alga is *Porphyridium aerugineum*.

24. The process of claim 23 wherein said artificial illumination has its energy content predominantly in the region of about 600 to 700 nanometers.

* * * * *